United States Patent [19]

Penny

[11] 4,182,446

[45] Jan. 8, 1980

[54] HEART VALVE HOLDER

[75] Inventor: William Penny, Arcadia, Calif.

[73] Assignee: Hancock Laboratories, Inc., Anaheim, Calif.

[21] Appl. No.: 914,534

[22] Filed: Jun. 12, 1978

[51] Int. Cl.² .................... B65D 85/50; B65D 81/22
[52] U.S. Cl. ........................................ 206/205; 3/1.5; 206/525
[58] Field of Search ............... 206/525, 205; 3/1.5

[56] References Cited

U.S. PATENT DOCUMENTS

| 2,880,856 | 4/1959 | Albrecht | 206/205 |
| 4,035,849 | 7/1977 | Angell et al. | 3/1.5 |

OTHER PUBLICATIONS

The Procurement and Preparation of Aortic Valve Homografts, Murray P. Sands, et al, Surgery, vol. 62, No. 5, pp. 839-842, Nov. 1967.

*Primary Examiner*—William T. Dixson, Jr.
*Attorney, Agent, or Firm*—Wayne R. Eberhardt

[57] ABSTRACT

This invention provides a holder which retains a natural tissue heart valve assembly during storage and transportation prior to implantation of the valve. The device includes an annular member circumscribing the heart valve assembly above the sewing ring thereof, and resilient arms which extend outwardly of the annular member and are connectable remote from the heart valve assembly. The device further includes resilient elements inclined outwardly for engaging the wall of a container receiving the heart valve holder and also may include a base member for supporting the base of the heart valve assembly and means releasably connecting said base member to said annular member so that the same are in spaced relationship.

22 Claims, 5 Drawing Figures

U.S. Patent
Jan. 8, 1980
4,182,446
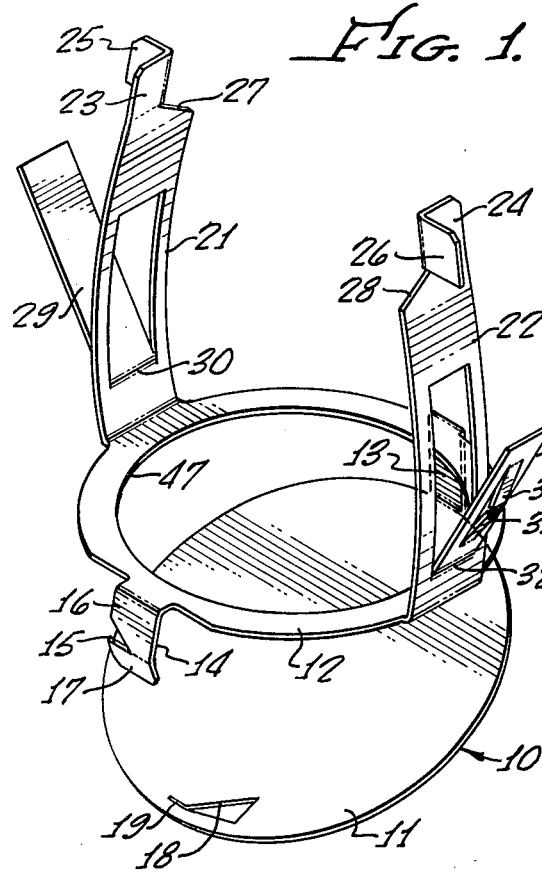
FIG. 1.
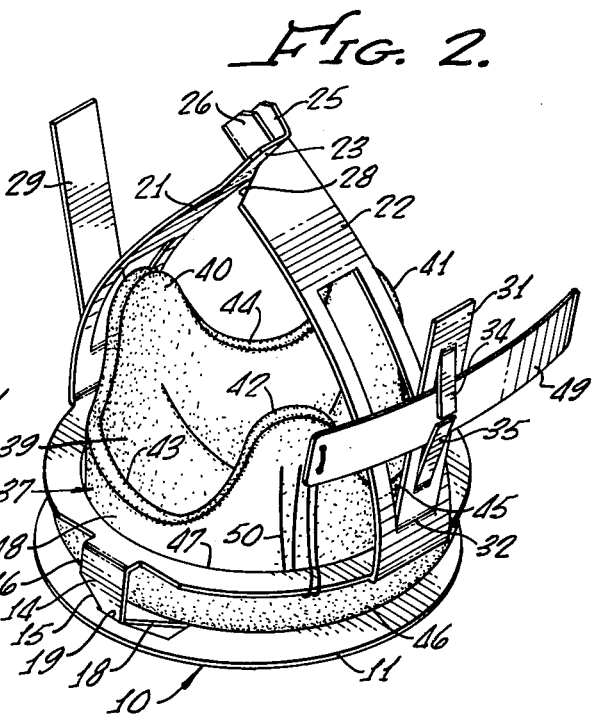
FIG. 2.
FIG. 3.
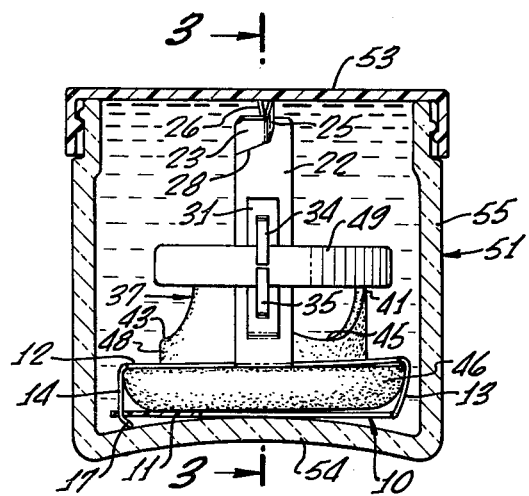
FIG. 4.
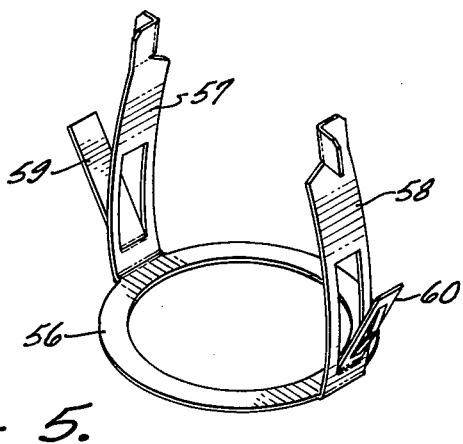
FIG. 5.

HEART VALVE HOLDER

BACKGROUND OF THE INVENTION

1. Field of the Invention

This invention pertains to a device for storing and retaining a natural tissue heart valve.

2. Description of the Prior Art

Heart valves taken from pigs, suitably processed, are used for implantation in human patients. These heart valves are mounted on a cloth-covered framework known as a stent, which includes projecting portions supporting the commissures of the heart valve, and arms which hold the margins of the cusps of the heart valve. From the base of this assembly projects a sewing ring for suturing int the annulus of the patient to attach the porcine valve in place of the removed diseased valve.

Prior to the implantation, the heart valve is fixed in a glutaraldehyde solution, which preserves the tissue. For shipment to hospitals where the valve is used, as well as for storage until time of use, it is conventional to position the valve in a jar or other container where the valve is immersed in a glutaraldehyde solution. To protect the valve, it is immobilized by means of a packing of rayon or other fibrous material. This may include rayon balls inserted into the cusps of the heart valve, frequently with a gauze wrapping around the valve. When the valve is to be used, the packing is removed and the valve is rinsed. Despite a thorough rinsing and washing, there is a possibility that some fiber of the packing may be retained on the valve. Even one fiber produces the danger that the patient's immune reactions will cause clotting around the fiber. The result can be fatal.

SUMMARY OF THE INVENTION

The present invention provides a holder for a natural tissue heart valve, which avoids the use of a packing of rayon or other material which includes fibers. As a result, it entirely avoids the problem of fiber retention on the heart valve, assuring that no fibers are present when the valve is inserted into the patient. The holder of this invention protects the heart valve while it is within the container, and facilitates the rinsing of the valve after it is removed and its preparation for implantation.

The heart valve holder is made of a resilient plastic and may include a base disc with an annular member positioned above it. The heart valve assembly is positioned on the base disc with the annular member above the sewing ring and circumscribing the upper portions of the heart valve assembly. Resilient arms extend outwardly from the annular member on the side opposite from the base member, being connectable at their outer ends. Elongated resilient tabs are inclined outwardly from the arm members.

The heart valve assembly, with the holder, are positioned in a container, such as a jar containing a glutaraldehyde solution. The tabs of the arm members bear against the sidewalls of the container, positioning the heart valve against lateral movement and preventing it from floating in the glutaraldehyde solution. The closure member of the container bears against the outer ends of the arms, deflecting them and pressing them inwardly. This positions the heart valve against movement vertically of the container. The base member rests against the bottom of the container and assures that there is no chafing of the bottom portion of the heart valve assembly along the bottom wall of the container. Removal from the container and rinsing are readily accomplished by gripping the outer ends of the arms of the holder. The base member and the annular member are released to pivot to an open position by separating a releasable tab, which permits the heart valve assembly to be removed in preparation for implantation.

BRIEF DESCRIPTION OF THE DRAWINGS

FIG. 1 is a perspective view of the heart valve holder of this invention prior to receiving a heart valve;

FIG. 2 is a perspective view of the heart valve holder, with the heart valve assembly in place and the holder in the closed position;

FIG. 3 is a longitudinal sectional view showing the heart valve assembly and the holder positioned within a storage and shipping container;

FIG. 4 is a longitudinal sectional view of the heart valve assembly and holder within the container, taken along line 4—4 of FIG. 3; and FIG. 5 is a perspective view of a modified form of the holder.

DESCRIPTION OF THE PREFERRED EMBODIMENT

The heart valve retainer 10 of this invention can be an integral member made from a sheet of resilient plastic material such as polypropylene 0.020 inch thick. The device includes a bottom circular disc 11 above which is a ring 12, connected to the disc 11 by an upstanding post 13. Opposite from the post 13, the ring 12 carries a depending tab 14, having a wedge-shaped notch 15 formed in one side edge 16. The outer end 17 of the tab 14, beyond the notch 15, is bent so as to incline inwardly. Beneath the tab 14 is a triangular opening 18 in the disc 11, from one apex of which extends a slit 19 in the material of the disc 11. The notch 15 in the tab 14 faces toward the slit 19.

Extending upwardly from the outer edge of the ring 12, on the side opposite from the base disc 11, are two resilient arms 21 and 22 which are located diametrically opposite from each other. These arms also are displaced 90° from the post 13 and tab 14, and extend both axially and radially outwardly from the ring. The upper end portions 23 and 24 of the arms 21 and 22 are bent outwardly. Inwardly of the upper end portions 23 and 24 wedge-shaped notches are formed in the arms 21 and 22, respectively, these notches facing in opposite directions. Short tabs 25 and 26 are bent outwardly along bend lines extending longitudinally of the arms 21 and 22 from the inner ends of the notches to the outer ends of the arms. The notches result in edge surfaces 27 and 28 inclining downwardly from the short tabs 25 and 26 to the longitudinal edges of the arms 21 and 22, respectively.

Above the ring 12 and below the notch 25 a U-shaped cut is formed in the arm 21, permitting an elongated tab 29 to be bent outwardly. The tab 29 is rectangular in shape and connected to the arm 21 at its bottom edge 30.

Similarly, a cut is formed in the arm 22 and an elongated tab 31 is bent outwardly of this arm. The tab 31 is of the same size as the tab 29, being rectangular in shape and attached to the arm 22 at its lower edge 32. In the central portion of the tab 31, parallel cuts are formed, along with an intermediate transverse cut, so as to produce two smaller tabs 34 and 35 which face toward each other.

In FIGS. 2, 3, and 4 a porcine heart valve assembly 37 is shown retained by the heart valve holder 10. The heart valve assembly 37 is of the general type illustrated in U.S. Pat. No. 3,570,014, being made up of a cloth-covered framework or stent of annular configuration, to the interior portions of which are attached a porcine heart valve 39. The commissures of the heart valve 39 are supported at the upwardly projecting portions 40, 41, and 42, while the margins of the cusps are secured at the intermediate portions 43, 44, and 45. At the bottom of the heart valve assembly 39 is a sewing ring 46, which is a cloth-covered ring of sponge material. This forms a thick flange that extends from the base of the heart valve assembly, later to be sutured to the annulus of the patient for attaching the heart valve assembly to the heart in the surgical procedure.

In associating the heart valve assembly 37 with the support device 10, the ring 12 is opened up by pivoting about the post 13, which acts as a hinge, and the base of the heart valve assembly is positioned on the upper surface of the disc 11. The ring 12 then is brought downwardly over the sewing ring 46 and the tab 14 is inserted into the triangular opening 18 in the disc 11. The tab 14 is advanced on the side of the notch 15 so that the material of the tab beyond the notch enters the slit 19 in the disc 11, which thereby frictionally retains the tab locked in the disc 11 with the straight side of the notch adjacent the undersurface of the disc. The periphery 47 of the ring 12 is of greater diameter than the outer periphery 48 of the heart valve assembly, so that the ring 12 fits readily over the heart valve assembly and the inner edge of the ring is spaced from the assembly. This helps assure that the material of the retainer does not directly contact any of the tissue of the heart valve assembly.

Next the arms 21 and 22 are brought together and interengaged so that the short tabs 27 and 28 are overlapped. This holds the arms together at their outer ends as shown in FIG. 2.

Customarily, the heart valve assembly will have an identification tag attached to it by a suture, such as the tag 49 which is secured to the assembly by a suture 50, later to be removed. The tag 49 is associated with the elongated tab 31 by being extended beneath the shorter opposed tabs 34 and 35. This effectively holds the identification tag, which is positioned so that its indicia faces outwardly.

The heart valve assembly and holder then are placed within a jar 51 where the unit is stored until time for use. The jar 51 contains a preserving and sterilizing solution, such as a glutaraldehyde solution 52. After the unit is placed in the jar, a screw-type lid 53 is fastened to the upper end of the jar. The height of the heart valve holder 10 in its free position (shown in phantom in FIG. 3), from the disc 11 to the upper ends of the arms 21 and 22, is greater than the interior height of the jar 51. Consequently, when the lid 53 is screwed onto the jar 51 it compresses the arms 21 and 22. This deflects these arms and causes them to press downwardly on the ring 12. This in turn, through the sewing ring 46 of the heart valve assembly, biases the bottom surface of the disc 11 against the bottom 54 of the jar. Thus, the support 10 and the heart valve assembly 37 are held against vertical movement in the jar 51, there being no clearance to permit such movement to take place.

The outwardly inclined elongated tabs 29 and 31 are spaced apart a distance greater than the interior diameter of the circumferential wall 55 of the jar 51 when these tabs are in their free position (indicated in phantom in FIG. 3). Consequently, as the unit is inserted into the jar, the tabs 29 and 31 are deflected inwardly. These tabs act as springs, serving to center the assembly within the jar and positioning it so that it is spaced from the circumferential wall 55. Consequently, there is no clearance for lateral movement of the support 10 and heart valve assembly 37, which are positioned against such movement within the jar. This protects the heart valve and precludes any possibility of its becoming damaged from vibration or other movement which might occur during the time the container is transported from one place to another.

By bearing against the sidewall 55, the tabs 29 and 31 create a frictional force which acts as a means to position the support 10 and heart valve assembly 37 vertically in the jar 51. Otherwise these elements would float in the glutaraldehyde solution, which could occur prior to attachment of the lid 53 or at the time of its removal. Even if the support 10 were to move upwardly in the jar, overcoming the frictional force, the amount of vertical movement would be limited to a very small distance. This is because the free outer ends of the tabs 29 and 31 would engage the annular shoulder 55a extending inwardly at the upper portion of the wall 55 just below where the threads of the jar are formed. The shoulder 55a then would serve as an abutment to preclude further upward movement.

When it is time to use the heart valve assembly 37, the lid 53 of the jar 51 is removed and the upper ends of the arms 21 and 22 are gripped by a suitable implement for removal of the support and heart valve assembly from the jar. It is not necessary to engage the heart valve assembly 37 as this takes place. Then the tab 14 may be removed from the disc 11, opening the ring 12 so that the heart valve assembly 37 may be dropped from the holder 10 into a rinsing solution. Alternatively, the outer ends of the arms 21 and 22 may be held while the heart valve is rinsed prior to being removed from the support 10. In either event, the rinsing operation is easily accomplished without injury to the heart valve assembly.

The embodiment of FIG. 5 is similar to the previously described embodiment, except that the base disc 11 is eliminated. This holder includes a ring 56 at opposite sides of which are upstanding arms 57 and 58 which are similar to the arms 21 and 22. Outwardly and upwardly inclined elongated tabs 59 and 60 project from the lower portions of the arms 57 and 58. The holder of FIG. 5 is used by positioning a heart valve assembly in the jar 51 with the base of the heart valve assembly resting on the bottom 54 of the jar. The ring 56 is positioned over the sewing ring of the heart valve assembly and the arms 57 and 58 are attached together. When the lid 53 of the jar is attached, the arms 57 and 58 are compressed and deflected, as in the previously described arrangement, causing the ring 56 to press downwardly on the sewing ring 46 and hold the heart valve against the bottom of the jar. The upwardly and outwardly inclined elongated tabs 59 and 60 bear against the circumferential wall 55 of the jar to prevent lateral movement. This embodiment is simpler to construct and does not require the operation of securing the ring of the holder to a base disc. However, placing the heart valve assembly within the jar and removing it from the jar are not as readily accomplished with the design of FIG. 5, nor is the rinsing operation as simple as where the unit 10 is used. With the base of the heart valve assembly engaging the bottom 54 of the jar, there is less assurance that the base of the valve assembly will be prevented from chafing on the jar.

The foregoing detailed description is to be clearly understood as given by way of illustration and example only, the spirit and scope of this invention being limited solely by the appended claims.

I claim:

1. A device for holding a natural tissue heart valve assembly comprising
    a base member adapted to support the base of a natural tissue heart valve assembly,
    an annular member adapted to circumscribe such a heart valve assembly above the sewing ring thereof,
    means for releasably securing said annular member in a spaced relationship above said base member,
    and arm means projecting upwardly from said annular member,
        said arms means including portions remote from said annular member adapted to engage one surface of a container receiving said heart valve holder when said base member engages an opposite surface of such container.

2. A device as recited in claim 1 in which said arm means includes two members projecting from diametrically opposite positions on said annular member, said two members having releasably interconnectable outer end portions.

3. A device as recited in claim 2 in which said arm means includes portions inclined outwardly of said annular member for engaging the sides of a container receiving said heart valve holder and positioning said heart valve holder within such a container.

4. A device as recited in claim 2 including a resilient element inclined outwardly from each of said two members for engaging the wall of a container receiving said heart valve holder and positioning said heart valve holder within said container.

5. A device as recited in claim 4 in which one of said resilient elements includes means for holding an identification tag of a heart valve.

6. A device as recited in claim 5 in which said means for holding an identification tag comprises a duality of tabs on said one resilient element, said tabs facing toward each other.

7. A device as recited in claim 1 in which said means for releasably securing said annular member in a spaced relationship above said base member includes
    a first member extending between said annular member and said base member on one side thereof,
    and tab means on the opposite side of said base member and said annular member for releasably connecting said base member and said annular member on said opposite side,
        said base member and said annular member being pivotal about said first member when said tab means is released for allowing a heart valve assembly to be associated with and to be removed from said heart valve holder.

8. A device as recited in claim 7 in which said base member includes an opening for receiving and frictionally gripping said tab means.

9. A device as recited in claim 7 in which said tab means includes a tab member depending from said annular member, and opening means in said base member for receiving said tab means and releasably holding the same.

10. A device as recited in claim 1 in which said base member is a substantially flat circular disc.

11. A device as recited in claim 1 in which said heart valve holder is an integral member of plastic sheet material.

12. A device as recited in claim 11 in which said plastic sheet material is polypropylene.

13. A holder for a natural tissue heart valve assembly comprising
    an annular member adapted to circumscribe such a heart valve assembly above the sewing ring thereof,
    a duality of arms,
        said arms projecting from one side of said annular member at diametrically opposite locations, said arms including interconnectable portions remote from said annular member,
    and a duality of resilient elements,
        each of said resilient elements extending axially and radially outwardly of said annular member on said one side thereof.

14. In combination with a natural tissue heart valve assembly including a base, a sewing ring and an outer peripheral surface above said sewing ring, and a container having a closure, a bottom wall opposite said closure and a sidewall between said closure and said bottom wall, a device for holding said heart valve assembly and positioning the same in said container comprising
    an annular member circumscribing said outer peripheral surface and overlying said sewing ring,
    and a resilient means extending from said annular member, said resilient means including,
        a first portion engaged and deflected by said closure so as to press downwardly on said annular member and position said heart valve assembly vertically in said container,
        and a second portion engaged and deflected by said sidewall so as to cause said annular member to position said heart valve assembly laterally in said container and so as to create a frictional force for resisting upward movement of said heart valve assembly relative to said container.

15. A device as recited in claim 14 in which said container includes an abutment, said abutment being engageable by said second portion for limiting upward movement of said heart valve assembly relative to said container.

16. In combination with a natural tissue heart valve assembly including a base, a sewing ring and an outer peripheral surface above said sewing ring, and a container having a closure, a bottom wall opposite said closure and a sidewall between said closure and said bottom wall, a device for holding said heart valve assembly and positioning the same in said container comprising
    a retaining means including
        a base member one side of which engages said bottom wall,
            said base of said heart valve assembly engaging the opposite side of said base member,
        and an annular member spaced above said base member, said annular member circumscribing said outer peripheral surface and overlying said sewing ring, and a resilient means extending from said retaining means, said resilient means including a first portion engaged and deflected by said closure so as to position said heart valve holder and said heart valve assembly vertically in said container, and a second portion engaged and deflected by said sidewall so as to position said heart valve holder and said heart valve assembly laterally in said container and so as to create a frictional force for resisting upward movement of said heart valve holder and said heart valve relative to said container.

17. A device as recited in claim 16 in which said annular member has a larger inside diameter than the diameter of said outer peripheral surface, whereby the inner edge of said annular member is spaced from said peripheral surface.

18. A device as recited in claim 16 in which said retaining means and said resilient means are made of plastic sheet material.

19. A device as recited in claim 16 in which said container includes a shoulder adjacent the upper end thereof, said second portion being engageable with said shoulder for precluding upward movement of said heart valve assembly relative to said container.

20. In combination with a natural tissue heart valve assembly including a base, a sewing ring and an outer peripheral surface above said sewing ring, and a container having a closure, a bottom wall opposite said closure and a sidewall between said closure and said bottom wall, a device for holding said heart valve assembly and positioning the same in said container comprising a base member one side of which engages said bottom wall, said base of said heart valve assembly engaging the opposite side of said base member, an annular member spaced above said base member, said annular member circumscribing said peripheral surface above said sewing ring, means interconnecting said base member and said annular member for selectively permitting separation of said base member and said annular member, a duality of resilient arms extending upwardly from opposite locations on said annular member, said closure member pressing downwardly on said arms so that said arms press downwardly on said annular member which through said sewing ring presses said base member against said bottom wall for thereby vertically positioning said heart valve holder and said heart valve assembly in said container, and a duality of resilient elements projecting upwardly and outwardly from said annular member, said resilient elements being on opposite sides of said annular member and having outer portions engaging said sidewall for thereby laterally positioning said heart valve holder and said heart valve assembly in said container and creating a frictional force resisting upward movement of said heart valve holder and heart valve assembly relative to said container.

21. A device as recited in claim 20 in which said container includes an annular shoulder adjacent the upper end thereof, and including a quantity of liquid in said container in which said heart valve holder and said heart valve assembly will float unless restrained, said outer portions of said resilient elements being engageable with said annular shoulder for preventing such floating of said heart valve holder and said heart valve assembly.

22. A device as recited in claim 20 in which said duality of resilient elements is formed by a tab inclined outwardly from each of said arms, the base of each of said tabs being connected to one of said arms.

* * * * *